(12) United States Patent
Doerr et al.

(10) Patent No.: US 8,774,934 B2
(45) Date of Patent: Jul. 8, 2014

(54) TEMPERATURE SENSOR FOR AN IMPLANTABLE MEDICAL APPARATUS

(75) Inventors: Thomas Doerr, Berlin (DE); Ingo Weiss, Berlin (DE)

(73) Assignee: Biotronik SE & Co. KG, Berlin (DE)

( * ) Notice: Subject to any disclaimer, the term of this patent is extended or adjusted under 35 U.S.C. 154(b) by 0 days.

(21) Appl. No.: 13/620,687

(22) Filed: Sep. 14, 2012

(65) Prior Publication Data

US 2013/0090707 A1    Apr. 11, 2013

Related U.S. Application Data (60) Provisional application No. 61/543,818, filed on Oct. 6, 2011.

(51) Int. Cl.
| A61N 1/05 | (2006.01) |
| A61B 5/05 | (2006.01) |
| A61N 1/36 | (2006.01) |
| A61N 1/37 | (2006.01) |
| A61N 1/08 | (2006.01) |

(52) U.S. Cl.
CPC ........... *A61N 1/3718* (2013.01); *A61N 1/36139* (2013.01); *A61N 1/056* (2013.01); *A61N 1/371* (2013.01); *A61N 2001/086* (2013.01); *A61N 1/36167* (2013.01)
USPC ............................... 607/62; 607/17; 600/547

(58) Field of Classification Search
USPC .......................................... 607/17, 62; 600/547
See application file for complete search history.

(56) References Cited

U.S. PATENT DOCUMENTS

| 4,901,725 | A  | * | 2/1990  | Nappholz et al. .............. 607/17 |
| 5,282,844 | A  | * | 2/1994  | Stokes et al. .................. 607/120 |
| 5,467,768 | A  | * | 11/1995 | Suda et al. .................... 600/391 |
| 5,630,426 | A  | * | 5/1997  | Eggers et al. ................. 600/547 |
| 6,681,135 | B1 |   | 1/2004  | Davis et al. |
| 7,260,481 | B1 | * | 8/2007  | Nakada .......................... 702/19 |
| 8,200,243 | B1 | * | 6/2012  | Feher ......................... 455/456.1 |
| 8,200,334 | B1 | * | 6/2012  | Min et al. ........................ 607/27 |
| 8,423,133 | B2 | * | 4/2013  | Doerr et al. ...................... 607/2 |
| 8,423,135 | B2 | * | 4/2013  | Doerr et al. ...................... 607/4 |
| 2007/0043404 | A1 | * | 2/2007  | Deimling ........................ 607/61 |
| 2008/0255642 | A1 | * | 10/2008 | Zarins et al. ................... 607/99 |
| 2009/0062873 | A1 | * | 3/2009  | Wu et al. .......................... 607/2 |
| 2009/0076409 | A1 | * | 3/2009  | Wu et al. ....................... 600/547 |
| 2010/0069921 | A1 | * | 3/2010  | Miller et al. .................. 606/130 |
| 2010/0138192 | A1 | * | 6/2010  | Min ................................ 703/1 |

(Continued)

OTHER PUBLICATIONS

European Search Report dated Jan. 15, 2013, 6 pages.

*Primary Examiner* — George Manuel
*Assistant Examiner* — Christopher A Flory
(74) *Attorney, Agent, or Firm* — ARC IP Law, PC; Joseph J. Mayo (57) ABSTRACT

A temperature sensor for detecting heating of at least one electrode pole of a temporarily or permanently implantable electrode line or a similar implant having at least one elongated electrical conductor which is connected to at least one electrode pole. The temperature sensor has an impedance detecting unit or is connected to one and is configured for evaluating an electrode pole impedance detected by the impedance detecting unit in such a manner that the evaluation takes place with respect to a temperature-dependent feature of the electrode impedance. The impedance detecting unit is electrically connected to the at least one electrode pole or is configured and arranged to be electrically connected to the at least one electrode pole.

15 Claims, 7 Drawing Sheets

(56) References Cited

U.S. PATENT DOCUMENTS

| | | | |
|---|---|---|---|
| 2011/0034979 A1* | 2/2011 | Min et al. | 607/116 |
| 2011/0034983 A1* | 2/2011 | Min et al. | 607/122 |
| 2011/0066028 A1 | 3/2011 | Min et al. | |
| 2011/0112599 A1* | 5/2011 | Zhang et al. | 607/37 |
| 2011/0118727 A1* | 5/2011 | Fish et al. | 606/33 |
| 2011/0144524 A1* | 6/2011 | Fish et al. | 600/547 |
| 2011/0160791 A1 | 6/2011 | Ellingson et al. | |
| 2012/0221086 A1* | 8/2012 | Wang | 607/116 |
| 2013/0073020 A1* | 3/2013 | Mouchawar et al. | 607/116 |
| 2013/0090707 A1* | 4/2013 | Doerr et al. | 607/62 |
| 2013/0123876 A1* | 5/2013 | Min | 607/37 |
| 2013/0226169 A1* | 8/2013 | Miller et al. | 606/34 |

* cited by examiner

TEMPERATURE SENSOR FOR AN IMPLANTABLE MEDICAL APPARATUS

This application claims the benefit of U.S. Provisional Patent Application 61/543,818 filed on 6 Oct. 2011, the specification of which is hereby incorporated herein by reference.

BACKGROUND OF THE INVENTION

1. Field of the Invention

At least one embodiment of the invention relates to a sensor for temperature changes at electrode poles, in particular electrode poles on an implantable stimulation electrode line for a heart stimulator, implantable pulse generator (IPG), cardioverter/defibrillator (ICD) or the like.

2. Description of the Related Art

Such implantable medical apparatuses are for example implantable defibrillators (ICDs) or heart pacemakers, which can emit electrical stimulation pulses via electrode lines to cardiac tissue (myocardium) or can detect electrical potentials in the heart tissue via adequate sensors. Other implants such as e.g. neurostimulators serve for stimulating other tissues. In connection with heart pacemakers it is know that they provide self-actingly automatic aftercare, e.g. as so-called cron jobs, i.e. perform self-tests which are preprogrammed with respect to sequence and time and during which, in accordance with today's guidelines, certain parameters such as e.g. stimulus threshold, electrode impedance, battery voltage, signal amplitudes etc. are detected. For this purpose, the test unit controlled by the control unit is used.

Implantable heart pacemakers or defibrillators are typically connected to electrode lines for the electrostimulation which have the disadvantage that the electrical conductor of the latter can heat up in a nuclear spin tomograph (also referred to as magnetic resonance tomograph) because the alternating magnetic fields present in the nuclear spin tomograph induce significant electrical currents in the electrical conductor. Also, such induced currents can be emitted via electrode poles of the electrode line to surrounding tissue and thus, for example, can cause undesirable heating of the tissue.

In fact, it is typical that at least one stimulation electrode line is connected to implantable heart pacemakers or defibrillators (hereinafter also designated as heart stimulators or IPGs (implantable pulse generator)), wherein said stimulation electrode line has a standardized electrical connector at its proximal end provided for connecting to the heart pacemaker or defibrillator and has one or a plurality of electrode poles at its distal end provided for placement in the heart. Such an electrode pole serves for emitting electrical pulses to the tissue (myocardium) of the heart and/or for sensing electrical fields so as to be able within the so-called sensing to sense an activity of a heart. For these purposes, electrode poles typically form electrically conductive surface sections of an electrode line. Electrode poles are typically provided as annular electrode in the form of a ring around the electrode line or in the form of a tip electrode at the distal end of the electrode line. The electrode poles are connected in an electrically conductive manner via one or a plurality of electrical conductors to contacts of the electrical connector of the electrode line at the proximal end of the electrode line. Thus, one or a plurality of electrical conductors run between the contacts of the electrical connector at the proximal end of the electrode line and the electrode poles at the distal end of the electrode line, wherein said electrical conductors electrically connect the one or a plurality of electrode poles to one or a plurality of the contacts. These electrical conductors can be used, on the one hand, for transmitting stimulation pulses to the electrode poles and, on the other, for transmitting electrical signals recorded by means of the electrode poles to the proximal end of the electrode line.

On the other hand, the electrode can also dissipate heat generated by currents induced in the electrode line to the surrounding body liquid or the surrounding tissue.

There are already different solutions in existence for reducing the MRT-induced electrode heating; however, primarily with modified electrodes. The temperature sensor, which is often required, is sometimes used.

Currently, the application of an MRT examination in case of patients with an IPG is contrainduced. The problems arising in the environment of the MRT are mainly heating of the electrode tip caused by the strong alternating electromagnetic magnetic field in the MRT.

Approaches to a solution relate primarily to the modification of the electrode; thus, e.g., the use of band-pass filters in the electrode is described. The disadvantages of such a solution, besides the constructional efforts, are primarily the interruption of the therapy-relevant electrode line with resistors, inductive and capacitive components and associated with that, a possible impairment of the therapy function such as, e.g., the emission of high-frequency signals (hemodynamic sensors, in short HDS, or closed loop stimulation, in short CLS, current pulses with steep edges, etc.). In addition, the reliability of the electrode line interrupted by the bandstop filter is reduced by the additional interfaces and thus, a potential source of errors for the failure of such an electrode is created.

BRIEF SUMMARY OF THE INVENTION

The disadvantage of the known solutions is the need of this special electrode with potentially disadvantageous implantation properties and long-term characteristics. Also, patients with lying standard electrodes (MR unsafe) cannot be retrofitted in an MR-compatible manner because also these special electrodes reveal the presence of standard electrodes as exclusion criterion. Even solutions that would be implemented within the implant require a sensor, which is problem, specifically a temperature sensor at the electrode tip. Integrating such a sensor likewise means designing a special electrode.

Many approaches, e.g. for reducing heating on electrode poles during a nuclear spin tomography (magnetic resonance tomography MRI), require a temperature sensor in order to identify such heating.

It is a feature of at least one embodiment of the invention to implement a safe MRT examination of patients having electronic implants.

This feature is achieved by a temperature sensor for detecting heating of at least one electrode pole of a temporarily or permanently implantable unit such as, for example, an electrode line having an elongated electrical conductor, wherein the temperature sensor has an impedance detecting device or is connected to one and is configured for evaluating an electrode pole impedance detected by the impedance detecting device in such a manner that the evaluation takes place with respect to a temperature-dependent feature of the electrode impedance. For this purpose, the impedance detecting device is electrically connected to at least one electrode pole or is configured and arranged to be electrically connected to the at least one electrode pole.

In one embodiment of the invention, the temperature sensor allows that the temperature detection can be carried out with a standard electrode because the measuring device can be located outside the electrode line, e.g. in the implant, and can be electrically connected via the usual contacts at the proximal end of an electrode line to the electrode poles of the electrode line. Thus, the disclosed technique makes it possible to carry out a temperature measurement only with measuring means within the implant and without the use of a special electrode (i.e. with integrated temperature measuring element).

Preferably, the temperature sensor is integral part of an implantable medical apparatus to which at least one electrode line with at least one electrode pole can be connected or is connected; i.e., one aspect of the invention relates to an implantable medical apparatus—in short: implant—with a temperature sensor according to at least one embodiment of the invention.

Preferably, such an implantable medical apparatus comprising a temperature sensor is additionally equipped with an adjusting device which, depending on the temperature-dependent feature of the electrode pole impedance, parameterizes an implant input circuit with respect to the electrode terminating impedance in such a manner that heating at the respective electrode pole is minimized.

This is made possible by a control method by means of which heating of the electrode tip in the nuclear spin tomograph (magnetic resonance tomograph, MRT) can be reduced. This control method is based on the approach to readjust the input impedance of the implant in such a manner that, according to the present circumstances (such as field distributions), the electrode connected thereto (without being per se MRI safe) is always terminated in terms of high frequency in such a manner that according to these circumstances, heating of the electrode tip is minimal.

Thus, the disclosed technique consists on the one hand of a sensor for temperature measurement and, on the other, a control method for effectively reducing the MRT-induced electrode heating, wherein the implant can achieve this object, namely largely independent of the connected electrode line. The implanted system equipped in such a manner is safe to the largest possible extent for use in the MRT.

In this connection, optionally based on a temperature measurement through adaptive changes of the implant properties with respect to the input impedance, the temperature sensor provides for the prerequisite to create favorable boundary conditions also for standard electrodes to minimize, according to the circumstances, heating of the electrode tips during a nuclear spin tomography (magnetic resonance tomography, MRI).

An implantable medical system, the integral part of which can be the temperature sensor, can comprise a single-polar or multi-polar temporarily usable catheter or a permanently implantable electrode line or an elongated electrically conductive implant having a partial insulation for which in each case local heating is to be expected, e.g. caused by currents induced within the MRT. In such system, the temperature sensor can be provided in one of the mentioned components or/and in an apparatus (implant, ablation generator, etc.) connected thereto, wherein the latter is preferred so as to be able, e.g., to use usual electrode lines.

Such a system allows a purely implant-side solution for the heating problem in the MRT. The temperature sensor utilized for controlling is made possible by means of a standard electrode and thus can be implemented in the implant alone, and the mechanism implemented in the form of an adjusting device for minimizing heat can be implemented by a suitably controlled implant input circuit in the implant.

Also disclosed is an alternative to such approaches that require a special electrode and thus can result in a significant cost reduction (development costs and manufacturing costs). Moreover, already implanted electrodes may be retrofitted as MRT-compatible system through exchange of the old implant with a new implant because no electrode extraction is necessary to be able to use any desired electrode combinations with the implant.

Preferably, the temperature sensor is configured to determine as the temperature-dependent feature of the impedance, the amount, phase, real part, imaginary part of the impedance or a combination of these variables, namely preferably for a predetermined frequency or a plurality of frequencies. The temperature sensor can also be configured to detect and evaluate a combination of these features for a plurality of electrode poles at the same time.

If the implantable medical apparatus is a heart stimulator equipped with an adequate impedance sensor for closed loop stimulation (CLS), such a CLS sensor can also serve as temperature sensor. In such a case, the continuous impedance measuring circuit of the CLS/HDS method already existing in the implant can be used for the temperature measurement.

With respect to the impedance detection, the following advantageous embodiment variants arise:

The impedance is determined by supplying/impressing a current as generator signal and measuring the resulting voltage.

The impedance is determined by supplying/impressing a voltage and measuring the resulting current.

The electrode pole impedance is preferably measured in a frequency range of 0.1 Hz-10 Hz.

The impedance detecting device is configured for filtering out measuring data prior to processing and only in certain frequency windows. A preferred frequency interval for this lies within 100 kHz and 10 MHz. All other frequency components of the measuring signal are preferably suppressed by a band-pass filter of the impedance detecting device.

The impedance detecting device or the temperature sensor is preferably configured to carry out the electrode impedance measurement at selected frequencies, namely preferably in each case in a discretely monofrequent manner, at least at one, preferably a plurality of frequencies/spectral lines of the impedance spectrum. According to a preferred embodiment variant, the impedance detecting device is configured to filter the respective individual measuring frequencies with a narrow band so as to suppress potential interferences in a particularly effective manner.

The impedance detecting device or the temperature sensor can comprise filters to detect the frequency, amplitudes and phase position of the generator signal, e.g. one or a plurality of corresponding PLL circuits.

The impedance detecting device can also be configured for filtering out measuring data prior to processing and only in certain time windows. Here, the time windows can be controlled by MRI signals. For this purpose, the implantable medical apparatus can have and use an MRT sensor that is configured to respond to the presence of MRT-typical magnetic fields and to generate an output signal that indicates the presence of MRT-typical magnetic fields. Alternatively or additionally, the time windows can be controlled by physiological signals, i.e. the impedance measurement takes place only in certain heart cycles or phases of a respective heart cycle. It is the object to thereby separate the impedance changes caused by temperature from the ones caused by the heart cycle/breathing cycle. For this purpose, the implantable medical apparatus may utilize any known adequate sensing units.

Preferably, the generator signal is a rectangular signal, wherein the impedance detecting device is configured for performing an evaluation of the impedance spectral lines at the harmonics of the generator signals.

For separating the temperature-related impedance changes from impedance changes caused in a different manner, e.g. physiologically, the temperature sensor may use a reference impedance curve which was recorded and stored during times in which no nuclear spin tomography took place. The temperature sensor may in particular be configured to regularly record new reference impedance curves and, for this purpose, may be connected to or equipped with an MRT sensor which is configured to respond to the presence of MRT-typical magnetic fields and to generate an output signal which indicates the presence of MRT-typical magnetic fields. In this case, the temperature sensor is configured to prevent recording and/or storing of reference impedance curves as long as the MRT sensor delivers an output signal indicating the presence of MRT-typical magnetic fields.

For separating a temperature-related impedance curve from impedance curves based on causes other than temperature-related causes, the temperature sensor may include morphology-based and adaptive filters.

According to a preferred embodiment variant, the adjusting device acts on an adjustable capacitor, an adjustable inductor, an adjustable resistor or a combination of such components in the input circuit or protective circuit of the implant. In particular, EMI capacitors or a portion thereof can be implemented (or connected in series or in parallel thereto) as a varicap; resistors as FET transistor. Inductances can be implemented by active components (e.g. transformation of a capacitance). Preferably, the adjusting device is configured to effect a voltage- and/or current-controlled adjustment (setting) of these elements depending on the temperature-related feature.

The adjusting device may be connected to a controller to which the temperature-dependent feature is fed as a sensor signal and which readjusts the adjusting device so as to minimize electrode pole heating. Preferably, the controller represents a control algorithm based on a gradient method, in particular for multi-dimensional controlling, i.e. tuning a combination of a plurality of elements of the input circuit such as capacitor, inductor and/or resistor.

The temperature sensor itself may be used as part of an MRT sensor or as MRT sensor, i.e. the output signal of the temperature sensor is used for determining the decision whether an electrode line or a catheter with one or a plurality of electrode poles is currently in the alternating magnetic field of the nuclear spin tomograph, i.e. whether an imaging sequence runs or not. A control unit of an implantable medical apparatus can be connected to such an MRT sensor and can be configured so as to switch the medical apparatus into a special MRI-designated operating mode in the event that the MRT sensor delivers a signal that indicates the presence of MRT-typical magnetic fields. This can take place in addition to the measure that the input circuit is parameterized such that the temperature development at the electrode pole is minimized.

The temperature sensor can also be part of a temperature signaling device in the MRT in that the output signal of the temperature sensor is used to indicate excessive electrode heating via a wireless interface to the MRT user, for example in case the tuning of the input circuit is not sufficient to reduce heating of the electrode pole as required. The wireless interface can be implemented in the form of a telemetry unit that may be configured for transmitting data in the MICS frequency band to an external apparatus. The MICS frequency band is a frequency band that is reserved for the communication with medical implants (MICS: medical implant communication service).

The aforementioned object is also achieved by the contribution of a method for setting an input impedance of an implantable medical apparatus for the connection of an electrode line having at least one elongated electrical conductor and at least one electrode pole connected to the conductor, the method comprising the following method steps:

detecting a temperature-related electrode impedance change and
  setting the input impedance such that the temperature-related electrode impedance change becomes as small as possible.

Further advantageous configurations arise from the combination of the above-described features and exemplary embodiments described below.

BRIEF DESCRIPTION OF THE DRAWINGS

The invention is now described in more detail by means of exemplary embodiments and with reference to the figures. In the figures.

DETAILED DESCRIPTION OF THE INVENTION

Figure 1:
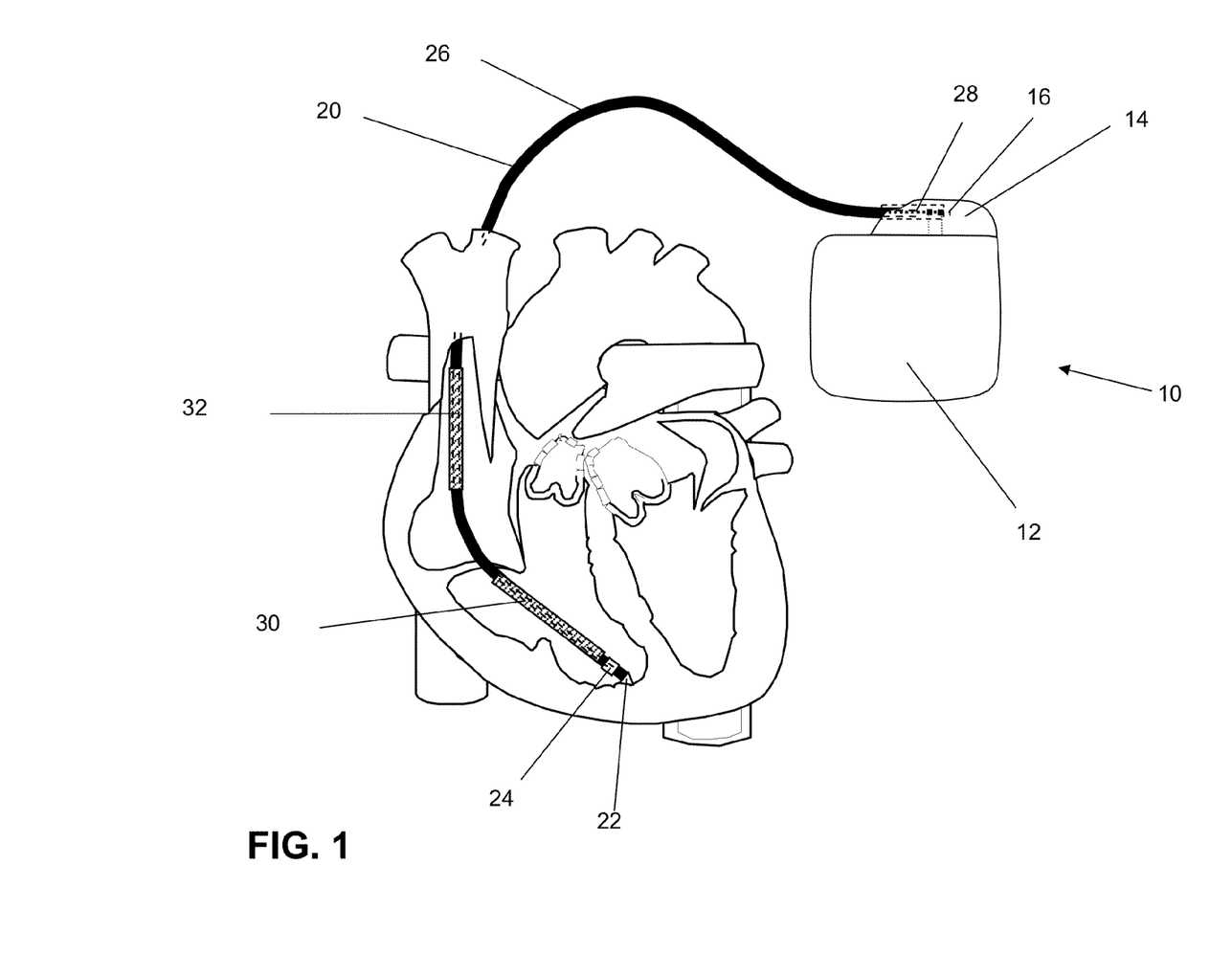
FIG. 1 shows as implantable medical apparatuses an implantable heart stimulator and an implantable electrode line connected thereto.

FIG. 1 illustrates an implantable medical apparatus in the form of an implantable heart stimulator 10 to which an electrode line 20 is connected, which has an elongated conductor.

The implantable heart stimulator 10 can be a heart pacemaker or a cardioverter/defibrillator (ICD). In the exemplary embodiment illustrated in FIG. 1, the heart stimulator 10 is a ventricular heart pacemaker and defibrillator. Other known heart stimulators are dual chamber heart pacemakers for stimulation of the right atrium and the right ventricle or biventricular heart pacemakers that, in addition to the right ventricle, can also stimulate the left ventricle.

Such stimulators typically have a housing 12, which usually is made of metal and thus is electrically conductive and can serve as large-area electrode pole. Typically, a connection housing 14, which is also designated as header, is fastened on the outer side of the housing 12. Such a header has typically contact sockets for receiving plug contacts. The plug contacts have electrical contacts 16 which are connected via suitable conductors to an electronics system arranged in the housing 12 of the heart stimulator 10.

In at least one embodiment of the invention, the electrode line 20 represents an implantable medical apparatus with an elongated electrical functional conductor. In a manner known per se, electrode poles in the form of a tip electrode 22 and an annular electrode 24 arranged in the vicinity of the latter are arranged at a distal end of the electrode line 20. The electrode poles 22 and 24 are configured such that depending on the function of a heart stimulator to which the electrode line 20 is connected, the electrode poles serve for sensing electrical potentials of the heart tissue (myocardium) or for emitting electrical signals, for example for emitting stimulation pulses to the heart tissue surrounding the electrode poles. FIG. 1 shows how the electrode poles, thus the tip electrode 22 and the annular electrode 24, in the case of use, the electrode 20, are located in the apex of a right ventricle of a heart.

The tip electrode 22 and the annular electrode 24 are each connected via at least one electrical conductor 26 to the contact of a plug connector 28 at the proximal end of the electrode line 20. The plug connector 28 has electrical contacts that communicate with the electrical contacts 16 of the contact socket in the connection housing 14 of the implantable heart stimulator.

The electrical conductors 26 in the electrode line 20 can be configured as approximately elongated cable pull conductors or as a helically wound conductors. Such conductors, which connect functional electrode poles to electrical contacts of the plug contact at the proximal end of the electrode line 20 in an electrically conductive manner, serve for transmitting electrical signals from the plug contact to the respective electrode pole or to direct sensed signals representing electrical potentials from the respective electrode pole to the plug contact.

The electrical conductors 26 which connect the electrode poles 22 and 24 to the electrical contacts of the plug connector 28 of the electrode line 20 are surrounded over the greater part of their length by an insulating shell so that an electrical contact to the tissue of the heart is achieved specifically via the electrode poles.

Besides the electrode poles 22 and 24 which typically serve for (in this case ventricular) stimulation of the heart tissue, the electrode line 20 comprises also two large-area electrode poles 30 and 32 which serve as defibrillation electrodes and are formed by at least one uninsulated helically wound wire.

It should be noted that the invention within the context of this exemplary embodiment is explained based on a right ventricular heart pacemaker and defibrillator. However, any other electro-medical device known per se, thus also a multi-chamber heart pacemaker or cardioverter/defibrillator (ICD) or also a neurostimulator or a pure monitoring implant can serve as medical device in the meaning of the invention. Also, the number of electrode lines which run from the implant to the stimulation site or sites and/or sensing sites can vary.

Figure 2:
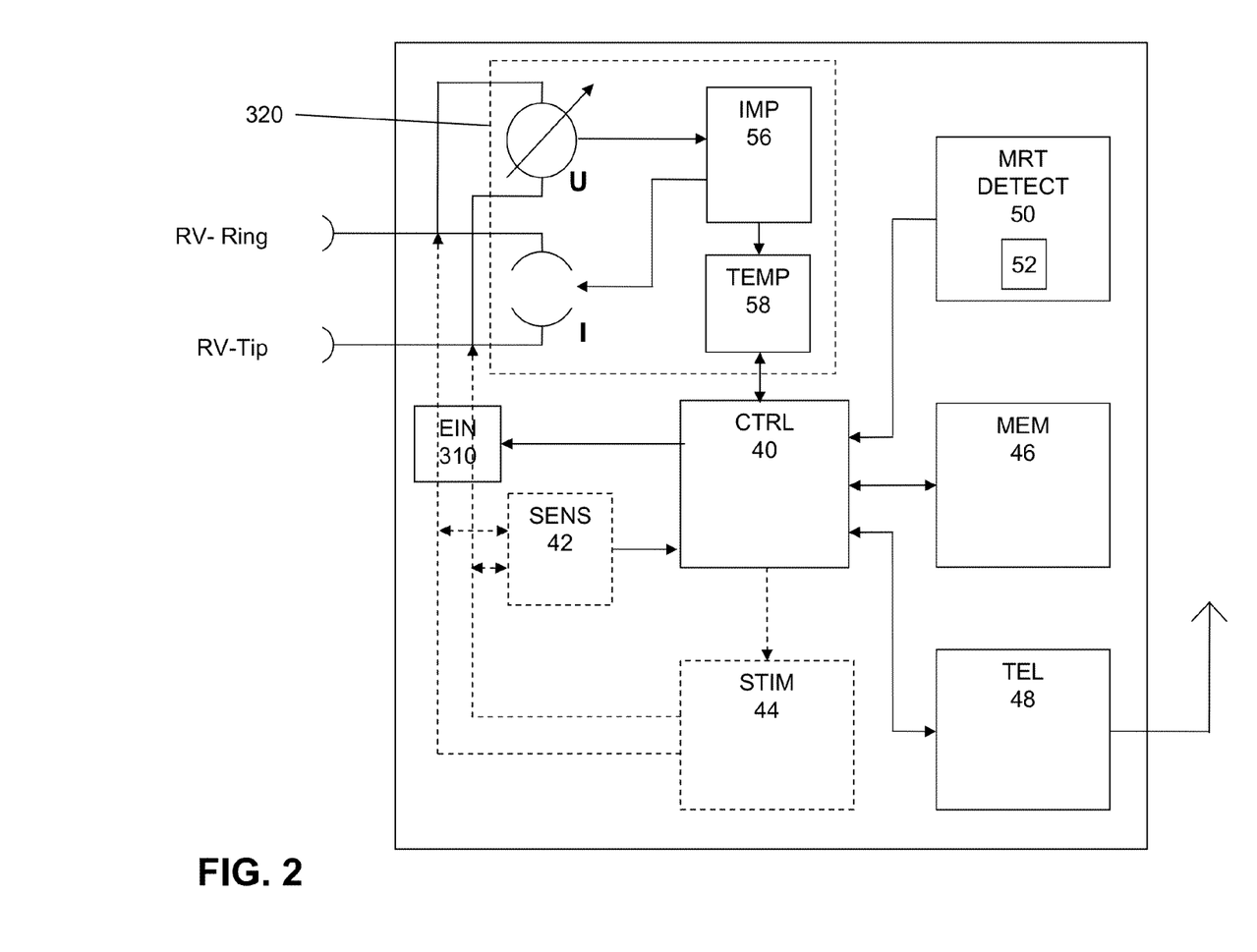
FIG. 2 shows some exemplary components of an implantable medical apparatus as illustrated for example in FIG. 1.

FIG. 2 shows exemplary and schematically some components of the heart stimulator 10 from FIG. 1. Typical components of such a heart stimulator are a control unit 40, one or a plurality of sensing units 42, each of which represents a diagnosis unit, and one or a plurality of stimulation units 44, each of which represent a therapy unit. The control unit 40 is initially connected to the sensing unit 42 as well as to the stimulation unit 44. The sensing unit 42 and the stimulation unit 44 are each connected to electrode connectors so as to be able, in case of the sensing unit 42, to detect electrical potentials of the heart tissue via the right ventricular annular electrode 24 and/or the right ventricular tip electrode 22 and, in case of the stimulation unit 44, to be able to output stimulation pulses, for example via the right ventricular annular electrode 24 and/or the right ventricular tip electrode 22.

Moreover, the control unit 40 is connected to a storage unit 46 for storing detected values of parameters to be measured in each case. A telemetry unit 48 which is also connected to the control unit 40 allows to transfer detected values of parameters to an external apparatus or to receive control commands from an external apparatus.

Moreover, the control unit 40 is connected to an MRT sensor 50 which is configured to detect MRT-typical magnetic fields and to output an output signal to the control unit 40 which signal indicates the presence of such MRT-typical magnetic fields. For this purpose, the MRT sensor 50 comprises a magnetic field sensor 52.

Alternatively, the MRT sensor can also be configured such that it detects voltages or voltage waveforms which result from a pulsed electromagnetic alternating field of the MRT and are induced into a programming coil (not shown) of the heart stimulator 10 and transmits an MRT detection signal to the control unit 40. The MRT sensor can be configured to respond to a field strength-dependent saturation behavior of the ferrite core.

Also, the MRT sensor 50 can be connected to a transformer having a ferrite core (not illustrated) which in turn is connected to an elongated electrical conductor, e.g. to the electrode line.

Furthermore, the control unit 40 is connected to an impedance determining unit 56. The impedance determining unit 56 is connected to a current source I and a voltage measuring unit U which in turn are connected to the connectors for the annular electrode 24 and the tip electrode 22. In this manner, the direct-current source I can constantly output current pulses via the tip electrode 22 and the annular electrode 24, and the voltage measuring unit can measure the voltage dropping in each case. From these values, the impedance determining unit 56 can determine a respective impedance value. The impedance determining unit 56 together with the direct-current source I and the voltage measuring unit U form an impedance detecting unit.

An impedance value determined by the impedance determining unit 56 depends on different influencing factors. For example, breaking of an electrical conductor in the electrode line 20 would be reflected in a very high impedance value. In case of an intact electrode line 20, the impedance to be measured between the electrode poles 22 and 24 depends also on the amount of blood in the right ventricle of a heart so that the impedance to be measured fluctuates cyclically corresponding to the heart cycle. For example, the impedance increases with decreasing blood volume, i.e. with decreasing volume of the right heart chamber so that a cyclical increase of the impedance indicates the cyclical contraction of the right heart chamber (right ventricle). Likewise, a corresponding increase of the measured impedance due to a chamber contraction after outputting a stimulation pulse can indicate the stimulation success. In this manner, the impedance determining unit 56 is able to carry out an automatic stimulation success control (automatic capture control; ACC).

The measured impedance depends also on the impedance of the electrode pole tissue contact. Thus, by evaluating the measured impedance values, an edema formation can be detected which can occur, for example, by heating the electrode pole due to alternating magnetic fields of a nuclear spin tomograph.

It is important in at least one embodiment of the invention that the impedance also depends on the temperature of the electrodes and the liquid surrounding the electrodes. The conductivity (sigma) of the liquid is temperature-dependent; for water-based electrolyte assumed here, a temperature coefficient of approximately 2%/K is considered. For the heating values to be expected, this can result in conductivity variations of well above 20%.

This effect is utilized by a temperature sensor 58 which is connected to the impedance determining unit 56 and evaluates the impedance signal, as described above and explained in detail in connection with FIG. 4, in order to deliver an electrode pole temperature-indicating temperature signal to the control unit 40.

It is to be noted that the impedance determining unit 56 can be connected not only indirectly to the control unit 40, as illustrated in FIG. 2, but in addition also directly and/or via a CLS evaluation unit.

The control unit, among other things, is configured to convert the temperature signal into a control signal for an input stage 310 of the implant 10 as shown in FIG. 2. The input stage 310 includes an input circuit that determines, among other things, the input impedance of the implant 10 relevant for the connected electrode lines. The input impedance is adjustable as explained above and explained below in more detail with reference to the FIGS. 5 and 6.

With respect to the input impedance of the input stage 310, the control unit implements a controller which is controlled by the temperature signal and is designed for setting the input impedance in such a manner, if possible, that the temperature-related impedance change is as small as possible, i.e. that heating of the electrode poles is as low as possible.

Figure 3:
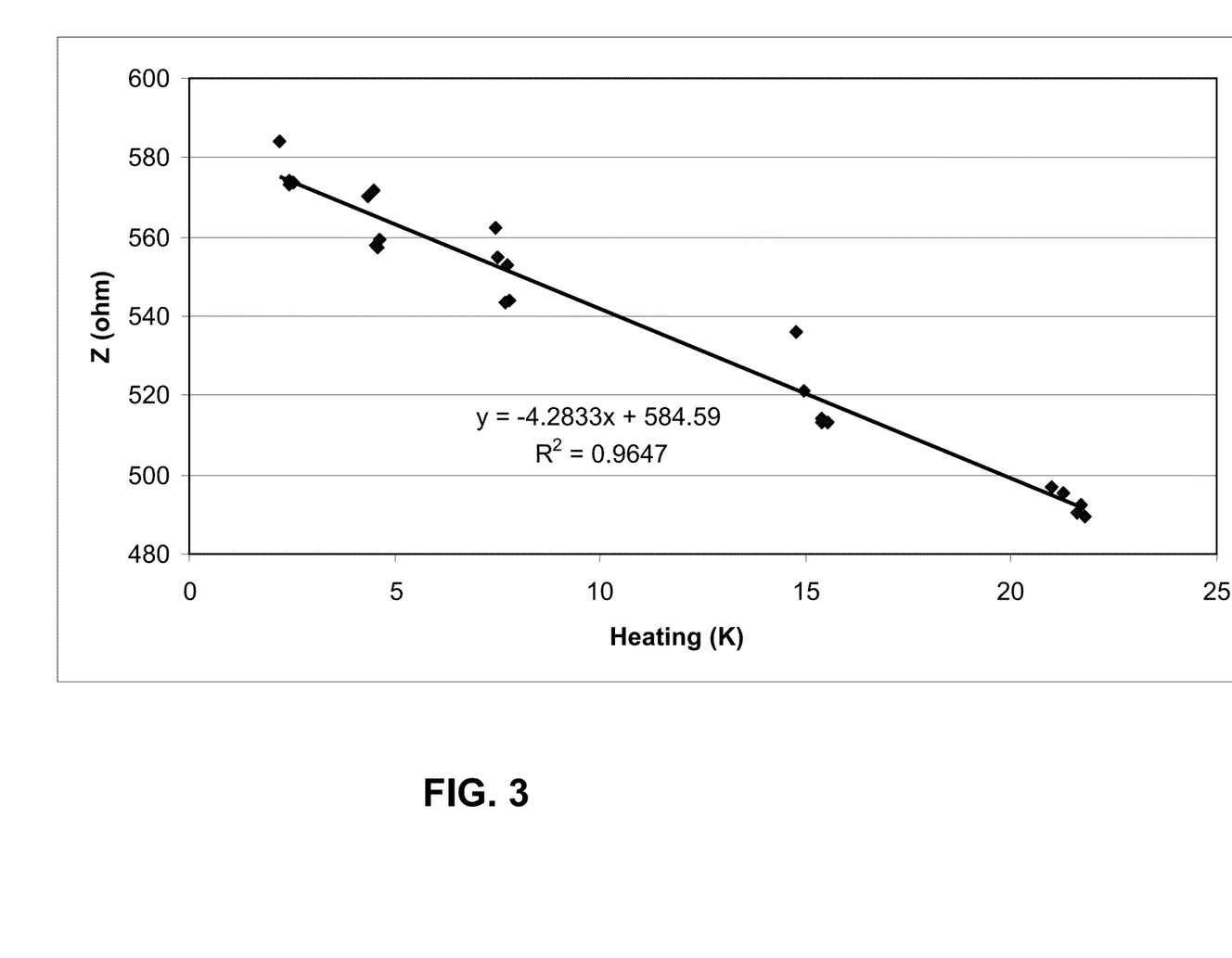
FIG. 3 shows the temperature dependency of the electrode pole impedance.

An example for the temperature dependency of the electrode impedance and evidence of the effectiveness is shown in FIG. 3. The measurements were made with sinusoidal generator signals at 10 kHz. The measuring medium is a convection-inhibiting gel according to standard ASTM F22182.

It is expected that a temperature increase of 15-20 K for a few seconds is tolerable without causing damage. During this time, a sufficient signal amplitude is to be achieved so that the controller can operate in a reliable and fault-tolerant manner.

Figure 4:
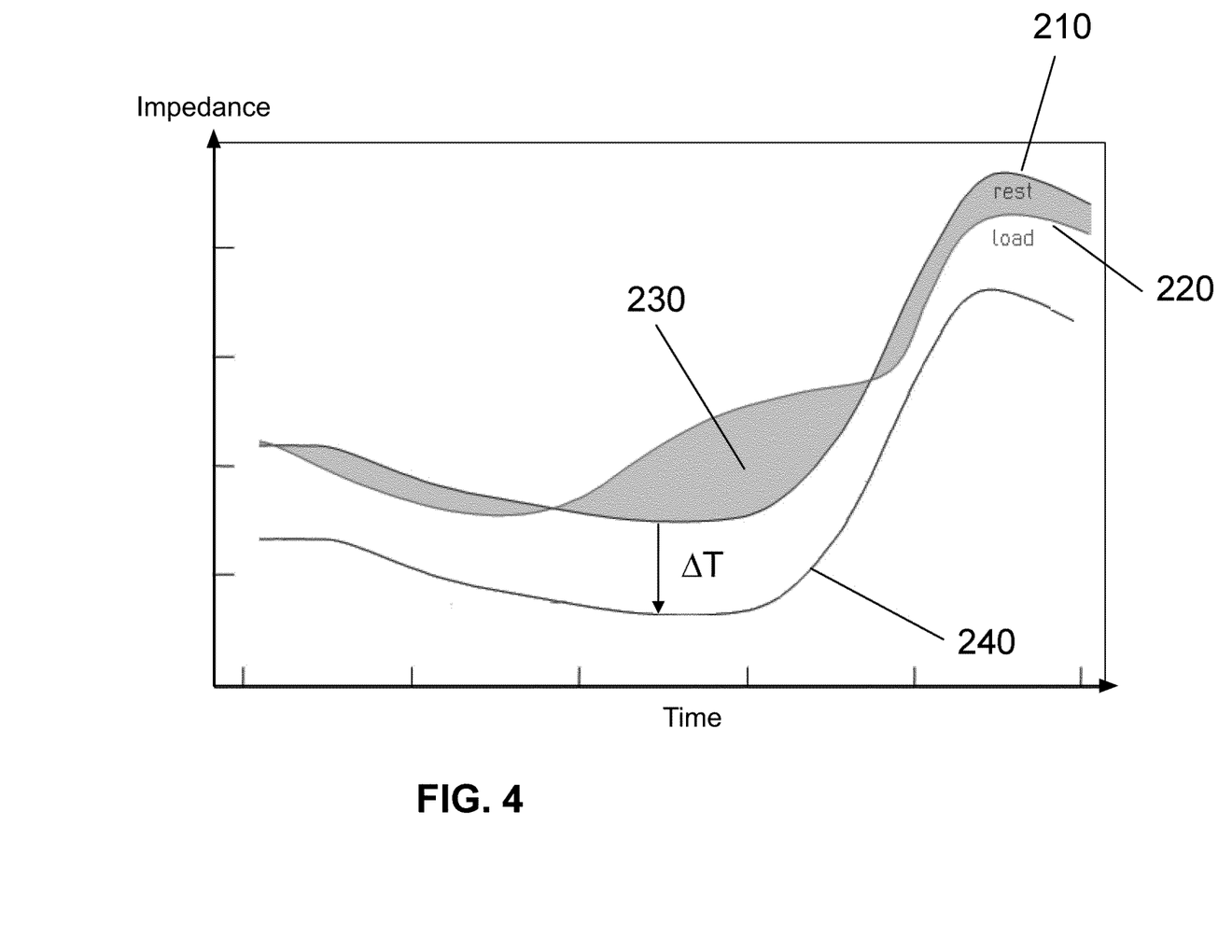
FIG. 4 shows a CLS useful signal compared to a CLS temperature signal.

In FIG. 4, the application example CLS shows the difference between the contractility value determined from the CLS signals and the temperature value, wherein the X Axis represents time and the Y axis the measured impedance. The contractibility is calculated from the difference area between two impedance curves (rest vs. load). The impedance curve 210 shows in an exemplary manner, the course of the unipolar intracardial impedance at the electrode tip in the state of rest and the curve 220 shows the same course of the impedance under load. The temperature difference becomes manifest in the offset of two comparable curves, e.g., curve 210 versus curve 240. It is well known that for evaluation for the CLS analysis or contractility analysis, the differential area 230 of both curves is evaluated and thus a measure for the contractility/metabolic requirement is determined which, for example, can be used for stimulation rate adaptation.

For the use of the impedance measuring function according to at least one embodiment of the invention, an evaluation of the absolute offset of the measuring curves is utilized in addition to the temperature measurement. Curve 240 shows the impedance curve to be expected in the state of rest at increased electrode tip temperature. According to the invention, the offset of the impedance curve with respect to a reference curve is now evaluated in an offset determining unit as a measure for the temperature and a correlation to the temperature increase ($\Delta T$) is established therefrom. Depending on the actual event sequence (Ax-Xx), the impedance reference curves recorded also for CLS can principally be considered as reference curves (reference courses); however, for the use according to at least one embodiment of the invention, different (shorter) time constants are assumed for updating the reference curves.

Figure 5:
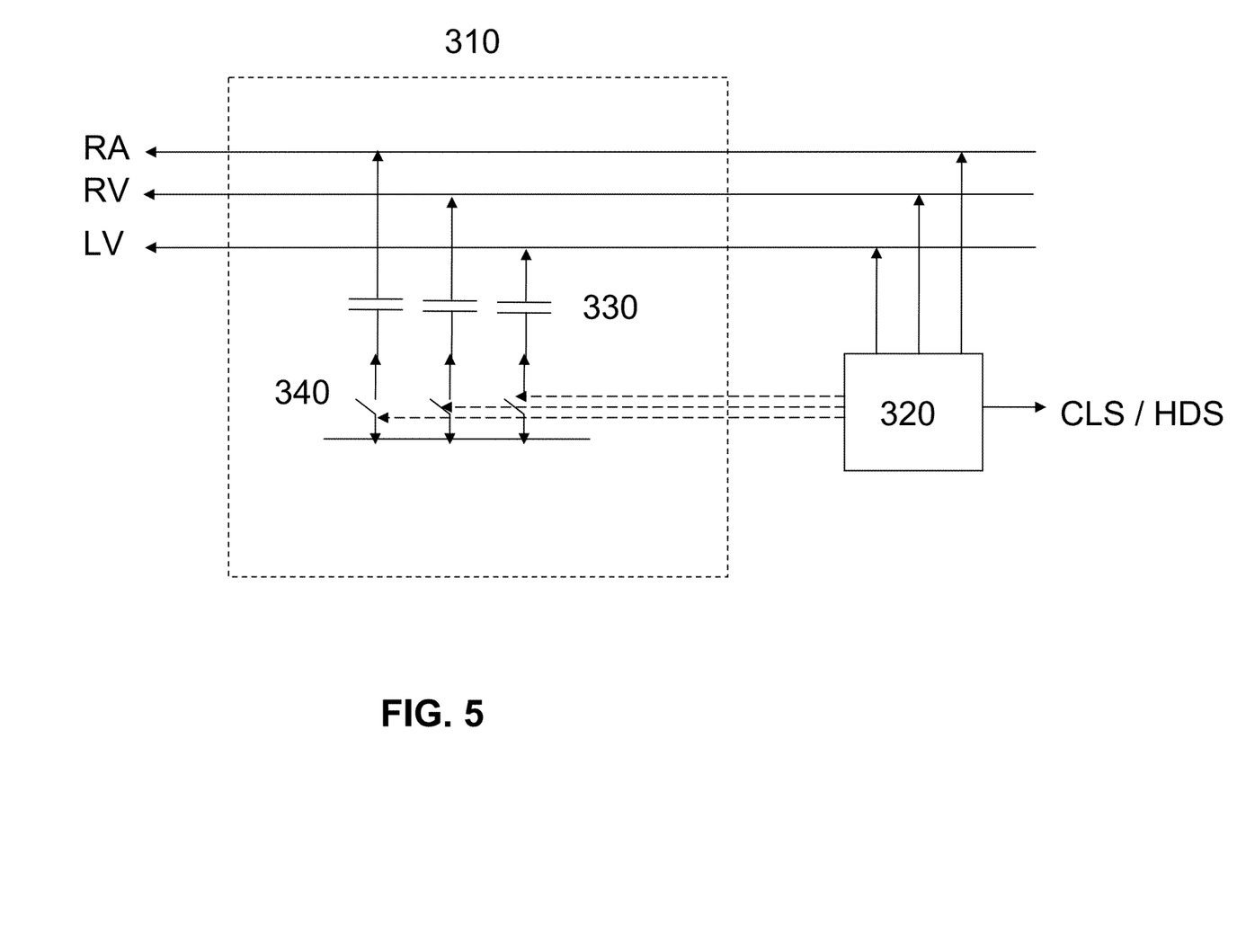
FIG. 5 shows a simplified block diagram of a first embodiment variant for the impedance evaluation unit.

FIG. 5 illustrates a simple block diagram for the device according to an embodiment of the invention. The electrode lines (here for a three-chamber heart stimulator with right atrial electrode line RA, right ventricular electrode line RV and left ventricular electrode line LV) are connected in the usual manner to an input stage 310 of the implant 10. The input stage 310 forms at least a part of an input circuit of the heart stimulator 10. Within the implant, one or all electrode lines are in turn connected to an impedance and temperature evaluation unit 320 expanded according to an embodiment of the invention which comprises the impedance measuring unit 56 and the temperature sensor 58 and which performs a continuous impedance measurement of the respective electrodes. Optionally, these signals are continued to be used also for CLS and/or HDS and/or LES evaluations (lung fluid sensor) in the implant 10 by the control unit 40 of the implant.

According to at least one embodiment of the invention, the impedance measuring stage 320 additionally evaluates the impedance curves according to FIG. 4 so that control information depending on the respective electrode temperature can be formed. This control information then prompts the impedance measuring unit to vary the characteristic of the input stage matching network 330 via an additional switching device 340 in such a manner that a reduction of the electrode pole temperature due to a detuning of the respective "electrode antenna characteristic" is achieved. This control principle functions independently of the type of electrode line used. The input stage matching network 330 comprises a plurality of capacitors which can be tuned or switched on or off by means of the switches 340 so that the input capacitance and thus the input impedance of the input stage 310 of the heart stimulator 10 can be adapted accordingly. The switching device 340 thus forms an adjusting device for the input impedance of the input stage 310.

Figure 6:
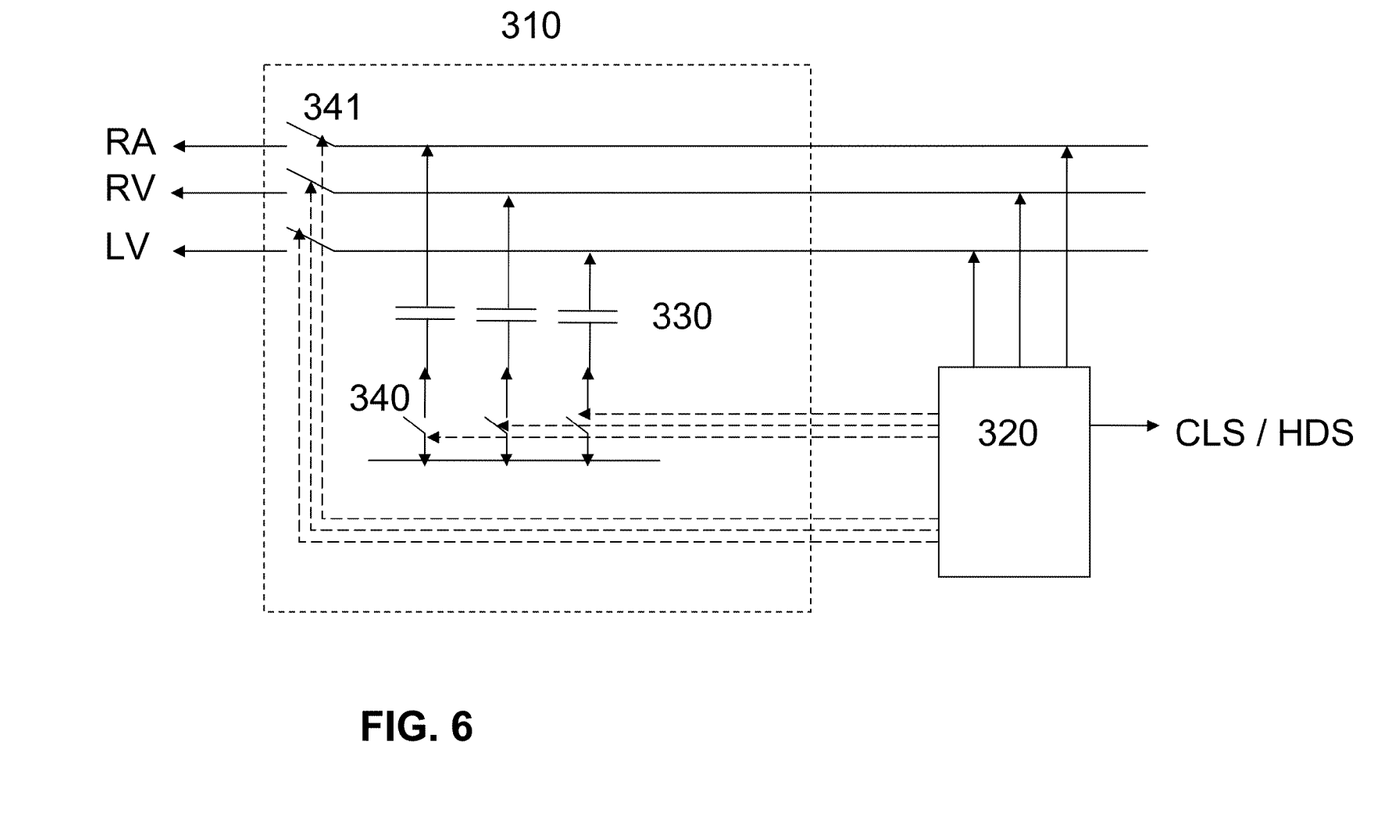
FIG. 6 shows a simplified block diagram of a second embodiment variant for the impedance evaluating unit with alternative or additional switches connected in series to the electrode lines.

According to a further embodiment variant illustrated in FIG. 6, alternatively or additionally, switches are installed in series to the electrode lines, wherein said switches can also connect or disconnect the terminating impedance of the electrode lines. In a particular embodiment, in particular in case of ICDs, these switches are implemented through the already existing protection transistors, which are preferably individually controllable.

Figure 7:
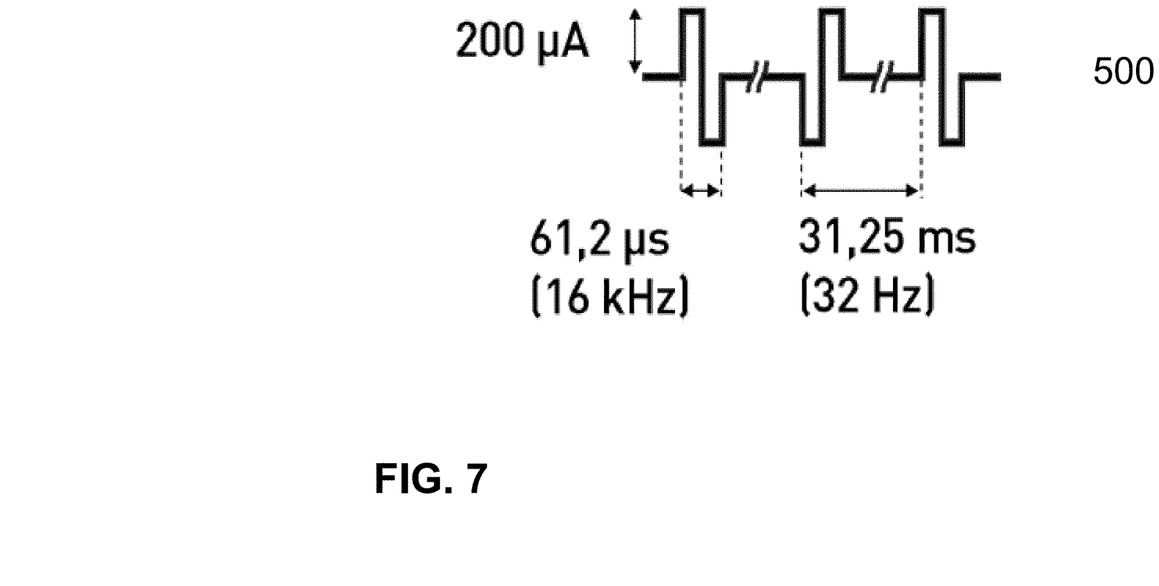
FIG. 7 shows a suitable generator signal for the impedance measurement.

FIG. 7 shows a usual generator signal 500 for impedance measurement. This signal is typically a constant current pulse sequence with an amplitude and pulse width well below the stimulus threshold of the tissue subjected to the generator signal.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. A temperature sensor configured to detect heating of at least one electrode pole of an implantable electrode line having at least one elongated electrical conductor which is connected to the at least one electrode pole, during a nuclear spin tomography or magnetic resonance tomography (MRT), comprising:
    an impedance detection unit that is
        part of said temperature sensor or
        is connected to said temperature sensor;
        wherein said impedance detection unit is configured to
            evaluate an electrode pole impedance detected by the
                impedance detection unit to detect a temperature-dependent feature or
change of the electrode pole impedance;
wherein the impedance detection unit is configured to be electrically connected to the at least one electrode pole;
a magnetic resonance tomography (MRT) sensor configured to respond to a presence of MRT-typical magnetic fields and to generate an output signal which indicates the presence of the MRT-typical magnetic fields; and
wherein the temperature sensor is configured to separate a temperature-related impedance curve from impedance curves based on causes other than temperature-related causes, through use of a reference impedance curve which was recorded and stored during times in which no nuclear spin tomography or magnetic resonance tomography (MRT) took place.

2. The temperature sensor according to claim 1, wherein the temperature sensor is integral part of an implantable medical apparatus to which at least one electrode line having said at least one electrode pole is connected.

3. An implantable medical apparatus with temperature sensor according to claim 2, wherein the implantable medical apparatus comprises an adjusting device that is configured to parameterize an implant input circuit with respect to the electrode impedance in such a manner that heating at a respective electrode pole is minimized based on the temperature-dependent feature or change of the electrode pole impedance.

4. The implantable medical apparatus according to claim 3, wherein the adjusting device comprises an adjustable capacitor, an adjustable inductor, an adjustable resistor or any combination thereof, in the implant input circuit of the implantable medical apparatus.

5. The implantable medical apparatus according to claim 4, wherein the adjusting device is connected to a controller to which the temperature-dependent feature or change is fed as a sensor signal and wherein said controller readjusts the adjusting device to minimize electrode pole heating.

6. The implantable medical apparatus according to claim 3, wherein the adjusting device is connected to a controller to which the temperature-dependent feature or change is fed as a sensor signal and wherein said controller readjusts the adjusting device to minimize electrode pole heating.

7. The temperature sensor according to claim 1, wherein the temperature sensor is configured to determine, an amount, phase, real part, imaginary part of impedance or any combination thereof as the temperature-dependent feature or change of the electrode pole impedance.

8. The temperature sensor according to claim 1, wherein the temperature sensor or the impedance detecting unit is configured to evaluate the electrode pole impedance only within one or a plurality of predetermined frequency ranges.

9. The temperature sensor according to claim 1, wherein the impedance detecting unit or the temperature sensor comprises filters configured to detect frequency, amplitudes and phase position of a supplied generator signal.

10. The temperature sensor according to claim 1, wherein the temperature sensor or the impedance detecting unit is configured to detect or evaluate electrode pole impedance only within an event-dependent time window.

11. The temperature sensor according to claim 10, wherein the event-dependent time window is controlled by a signal feature or event reoccurring within successive heart cycles.

12. The temperature sensor according to claim 11, wherein the event-dependent time window is controlled by the MRT sensor.

13. The temperature sensor according to claim 10, wherein the event-dependent time window is controlled by the MRT sensor.

14. The temperature sensor according to claim 1, wherein the temperature sensor is configured to determine a combination of one or more of an amount, phase, real part, imaginary part of impedance as the temperature-dependent feature or change of the electrode pole impedance for a plurality of electrode poles at the same time.

15. A method of utilizing a temperature sensor configured to detect heating of at least one electrode pole of an implantable electrode line having at least one elongated electrical conductor which is connected to the at least one electrode pole, during a nuclear spin tomography or magnetic resonance tomography (MRT), comprising:
utilizing an impedance detection unit that is
part of said temperature sensor or
is connected to said temperature sensor, in
evaluating an electrode pole impedance detected by the impedance detection unit to detect
a temperature-dependent feature or
change of the electrode pole impedance
wherein the impedance detection unit is configured to be electrically connected to the at least one electrode pole;
utilizing a magnetic resonance tomography (MRT) sensor, wherein said MRT sensor is configured to respond to a presence of MRT-typical magnetic fields and to generate an output signal which indicates the presence of the MRT-typical magnetic fields; and
wherein the temperature sensor is configured to separate a temperature-related impedance curve from impedance curves based on causes other than temperature-related causes, through use of a reference impedance curve which was recorded and stored during times in which no nuclear spin tomography or magnetic resonance tomography (MRT) took place.

* * * * *